(12) United States Patent
Locke

(10) Patent No.: US 12,070,545 B2
(45) Date of Patent: Aug. 27, 2024

(54) WOUND THERAPY SYSTEM WITH CONDUIT BLOCKAGE DETECTION

(71) Applicant: KCI LICENSING, INC., San Antonio, TX (US)

(72) Inventor: Christopher B. Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 354 days.

(21) Appl. No.: 17/259,273

(22) PCT Filed: Jul. 10, 2019

(86) PCT No.: PCT/US2019/041244
§ 371 (c)(1),
(2) Date: Jan. 11, 2021

(87) PCT Pub. No.: WO2020/018328
PCT Pub. Date: Jan. 23, 2020

(65) Prior Publication Data
US 2021/0275737 A1    Sep. 9, 2021

Related U.S. Application Data

(60) Provisional application No. 62/698,405, filed on Jul. 16, 2018.

(51) Int. Cl.
*A61M 1/00* (2006.01)

(52) U.S. Cl.
CPC ............. *A61M 1/96* (2021.05); *A61M 1/962* (2021.05); *A61M 1/92* (2021.05); *A61M 2205/18* (2013.01);
(Continued)

(58) Field of Classification Search
CPC .......... A61M 1/96; A61M 1/962; A61M 1/92; A61M 2205/18; A61M 2205/3344;
(Continued)

(56) References Cited

U.S. PATENT DOCUMENTS 1,355,846 A   10/1920  Rannells
2,547,758 A    4/1951  Keeling
(Continued)

FOREIGN PATENT DOCUMENTS

AU    550575 B2    3/1986
AU    745271 B2    3/2002
(Continued)

OTHER PUBLICATIONS

International Search Report in International Application No. PCT/US2019/041244, mailed on Dec. 4, 2019.
(Continued)

*Primary Examiner* — Susan S Su
*Assistant Examiner* — Eric Rassavong

(57) ABSTRACT

A wound therapy system includes a canister configured to contain fluid removed from a wound site, a primary conduit having a first end coupled to the canister and a second end coupled to the wound site, and a pump fluidly coupled to the wound site via the primary conduit. The pump is configured to apply negative pressure to the wound site via the primary conduit. The system includes a pressure indicator configured to indicate a negative pressure at the pressure indicator and a secondary conduit having a first end coupled to the pressure indicator and a second end coupled to the wound site such that the negative pressure at the wound site is fluidly transmitted to the pressure indicator via the secondary conduit. A blockage in the primary conduit causes the negative pressure indicated by the pressure indicator to differ from the negative pressure applied by the pump.

19 Claims, 8 Drawing Sheets

(52) U.S. Cl.
CPC ............... *A61M 2205/3344* (2013.01); *A61M 2205/3553* (2013.01); *A61M 2205/502* (2013.01); *A61M 2205/584* (2013.01); *A61M 2205/75* (2013.01)

(58) Field of Classification Search
CPC .... A61M 2205/3553; A61M 2205/502; A61M 2205/584; A61M 2205/75; A61M 2205/3355; A61M 2205/3569; A61M 2205/702
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2011/0288535 A1* | 11/2011 | Locke | A61M 1/966 137/15.01 |
| 2012/0271256 A1* | 10/2012 | Locke | A61M 1/962 604/319 |
| 2013/0218109 A1* | 8/2013 | Chen | A61M 1/98 604/319 |
| 2014/0100518 A1* | 4/2014 | Baxter | A61M 3/022 604/93.01 |
| 2015/0165182 A1* | 6/2015 | Pratt | A61M 39/22 604/290 |
| 2016/0256614 A1 | 9/2016 | Hall et al. | |
| 2017/0028111 A1* | 2/2017 | Tumey | A61M 1/96 |
| 2019/0201599 A1* | 7/2019 | Chang | A61M 1/80 |
| 2019/0385434 A1* | 12/2019 | Yuds | A61M 1/34 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2 626 049 A1 | 8/2013 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |

(56) References Cited

FOREIGN PATENT DOCUMENTS

| WO | 80/02182 A1 | 10/1980 | | |
|---|---|---|---|---|
| WO | 87/04626 A1 | 8/1987 | | |
| WO | 90/010424 A1 | 9/1990 | | |
| WO | 93/009727 A1 | 5/1993 | | |
| WO | 94/020041 A1 | 9/1994 | | |
| WO | 96/05873 A1 | 2/1996 | | |
| WO | 97/18007 A1 | 5/1997 | | |
| WO | 99/13793 A1 | 3/1999 | | |
| WO | WO-2012/145543 A1 | 10/2012 | | |
| WO | WO-2013078214 A1 | * | 5/2013 | ............ A61M 1/602 |
| WO | WO-2013123022 A1 | * | 8/2013 | ....... A61F 13/00068 |
| WO | WO-2017062042 A1 | * | 4/2017 | .......... A61M 1/0088 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 pages English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

WOUND THERAPY SYSTEM WITH CONDUIT BLOCKAGE DETECTION

CROSS-REFERENCE TO RELATED APPLICATIONS

This application claims the benefit of priority to international patent application number PCT/US2019/041244, filed on Jul. 10, 2019, which claims the benefit of priority to U.S. Provisional Application No. 62/698,405, filed on Jul. 16, 2018, the complete disclosures of which are hereby incorporated herein by reference in their entireties.

BACKGROUND

The present disclosure relates generally to a wound therapy system, and more particularly to a wound therapy system that provides negative pressure wound therapy.

Negative pressure wound therapy (NPWT) is a type of wound therapy that involves applying a negative pressure to a wound site to promote wound healing. Some wound treatment systems apply negative pressure to a wound using a pneumatic pump to generate the negative pressure and flow required.

SUMMARY

One implementation of the present disclosure is a wound therapy system. The wound therapy system includes a canister configured to contain fluid removed from a wound site, a primary conduit having a first end coupled to the canister and a second end coupled to the wound site, and a pump fluidly coupled to the wound site via the primary conduit. The pump is configured to apply negative pressure to the wound site via the primary conduit. The system includes a pressure indicator configured to indicate a negative pressure at the pressure indicator and a secondary conduit having a first end coupled to the pressure indicator and a second end coupled to the wound site such that the negative pressure at the wound site is fluidly transmitted to the pressure indicator via the secondary conduit. A blockage in the primary conduit causes the negative pressure indicated by the pressure indicator to differ from the negative pressure applied by the pump.

In some embodiments, the canister includes a first chamber configured to contain the fluid removed from the wound site and a second chamber fluidly isolated from the first chamber. The pressure indicator may be located within the second chamber.

In some embodiments, the second chamber is configured to controllably leak air into the second chamber, causing the negative pressure at the pressure indicator to equilibrate to atmospheric pressure after the blockage occurs.

In some embodiments, the second chamber is configured to controllably leak air into the second chamber at a controlled leak rate. The pump may be configured to remove the air from the second chamber via the secondary conduit and the primary conduit at an air removal rate greater than the controlled leak rate, causing the negative pressure at the pressure indicator to be substantially equal to the negative pressure applied by the pump before the blockage occurs.

In some embodiments, the wound therapy system includes a filter located along a wall of the second chamber. The filter can be configured to controllably leak air into the second chamber.

In some embodiments, the wound therapy system includes a filter coupled to the first end of the secondary conduit proximate the canister. The filter can be configured to controllably leak air into the secondary conduit.

In some embodiments, the pressure indicator is configured to physically deform or collapse responsive to the negative pressure at the pressure indicator. In some embodiments, the pressure indicator includes a plurality of individual sub-indicators. Each of the sub-indicators may be configured to physically deform or collapse at a different negative pressure such that the negative pressure at the pressure indicator is indicated by which of the sub-indicators are physically deformed or collapsed. In some embodiments, each of the sub-indicators has a different thickness, causing each of the sub-indicators configured to physically deform or collapse at a different negative pressure.

In some embodiments, the pressure indicator includes at least one of a bellows, a dial indicator, a holographic indicator, or a spring-biased extensible indicator.

In some embodiments, the pressure indicator is configured to indicate the negative pressure at the pressure indicator relative to a plurality of pressure thresholds. In some embodiments, the plurality of pressure thresholds include at least a low pressure threshold and a high pressure threshold such that the pressure indicator indicates whether the negative pressure at the pressure indicator is within a first negative pressure range below the low pressure threshold, within a second negative pressure range between the low pressure threshold and the high pressure threshold, and within a third negative pressure range above the high pressure threshold.

In some embodiments, each of the negative pressure ranges corresponds to a different color visible on the pressure indicator such that the pressure indicator indicates a first color when the negative pressure at the pressure indicator is within the first negative pressure range, a second color when the negative pressure at the pressure indicator is within the second negative pressure range, and a third color when the negative pressure at the pressure indicator is within a third negative pressure range.

In some embodiments, the pressure indicator is an electronic pressure sensor coupled to the first end of the secondary conduit proximate the canister and configured to sense the negative pressure within the secondary conduit.

In some embodiments, the wound therapy system includes a bacterial filter located between the pressure indicator and the secondary conduit.

In some embodiments, the pressure indicator includes a wireless communications interface configured to transmit pressure measurements recorded by the pressure indicator to an external system or device.

In some embodiments, the pressure indicator is configured to compare the negative pressure at the pressure indicator to one or more pressure thresholds and generate an alarm based on the negative pressure at the pressure indicator relative to one or more pressure thresholds.

In some embodiments, the pressure indicator includes a wireless communications interface and is configured to transmit the alarm to an external system or device via the wireless communications interface.

In some embodiments, the pressure indicator includes a user interface and is configured to present the alarm to a user via the user interface. In some embodiments, the user interface includes at least one of an electronic display configured to present the alarm visually or a speaker or sounder configured to present the alarm aurally.

Another implementation of the present disclosure is a method for detecting a blockage in a wound therapy system. The method includes containing fluid removed from a wound site within a canister, coupling a first end of a primary conduit to the canister and a second end of the primary conduit to the wound site, operating a pump fluidly coupled to the wound site via the primary conduit to apply negative pressure to the wound site via the primary conduit, coupling a first end of a secondary conduit to a pressure indicator and a second end of the secondary conduit to the wound site such that the negative pressure at the wound site is fluidly transmitted to the pressure indicator via the secondary conduit, using the pressure indicator to indicate a negative pressure at the pressure indicator, and detecting the blockage in response to the negative pressure indicated by the pressure indicator differing from the negative pressure applied by the pump.

In some embodiments, the method includes containing the fluid removed from the wound site within a first chamber of the canister and locating the pressure indicator within a second chamber of the canister isolated from the first chamber.

In some embodiments, the method includes controllably leaking air into the second chamber, causing the negative pressure at the pressure indicator to equilibrate to atmospheric pressure after the blockage occurs.

In some embodiments, the air controllably leaks into the second chamber at a controlled leak rate. Operating the pump may remove the air from the second chamber via the secondary conduit and the primary conduit at an air removal rate greater than the controlled leak rate, causing the negative pressure at the pressure indicator to be substantially equal to the negative pressure applied by the pump before the blockage occurs.

In some embodiments, the method includes locating a filter along a wall of the second chamber controllably leaking air into the second chamber via the filter.

In some embodiments, coupling a filter to the first end of the secondary conduit proximate the canister and controllably leaking air into the secondary conduit via the filter.

In some embodiments, the pressure indicator indicates the negative pressure at the pressure indicator by physically deforming or collapsing responsive to the negative pressure at the pressure indicator.

In some embodiments, the pressure indicator includes a plurality of individual sub-indicators. Each of the sub-indicators may be configured to physically deform or collapse at a different negative pressure. The pressure indicator may indicate the negative pressure at the pressure indicator by physically deforming or collapsing one or more of the sub-indicators.

In some embodiments, each of the sub-indicators has a different thickness, causing each of the sub-indicators configured to physically deform or collapse at a different negative pressure.

In some embodiments, the pressure indicator includes at least one of a bellows, a dial indicator, a holographic indicator, or a spring-biased extensible indicator.

In some embodiments, the pressure indicator indicates the negative pressure at the pressure indicator relative to a plurality of pressure thresholds. In some embodiments, the plurality of pressure thresholds include at least a low pressure threshold and a high pressure threshold such that the pressure indicator indicates whether the negative pressure at the pressure indicator is within a first negative pressure range below the low pressure threshold, within a second negative pressure range between the low pressure threshold and the high pressure threshold, and within a third negative pressure range above the high pressure threshold.

In some embodiments, each of the negative pressure ranges corresponds to a different color visible on the pressure indicator such that the pressure indicator indicates a first color when the negative pressure at the pressure indicator is within the first negative pressure range, a second color when the negative pressure at the pressure indicator is within the second negative pressure range, and a third color when the negative pressure at the pressure indicator is within a third negative pressure range.

In some embodiments, the pressure indicator is an electronic pressure sensor coupled to the first end of the secondary conduit proximate the canister senses the negative pressure within the secondary conduit.

In some embodiments, the method includes locating a bacterial filter between the pressure indicator and the secondary conduit.

In some embodiments, the method includes transmitting pressure measurements recorded by the pressure indicator to an external system or device via a wireless communications interface of the pressure indicator.

In some embodiments, the method includes comparing the negative pressure at the pressure indicator to one or more pressure thresholds and generating an alarm based on the negative pressure at the pressure indicator relative to one or more pressure thresholds.

In some embodiments, the method includes transmitting the alarm to an external system or device via a wireless communications interface of the pressure indicator.

In some embodiments, the method includes presenting the alarm to a user via a user interface of the pressure indicator.

In some embodiments, presenting the alarm to the user includes at least one of presenting the alarm visually via an electronic display of the user interface or presenting the alarm aurally via a speaker or sounder of the user interface.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Wound Therapy System

Figure 1:
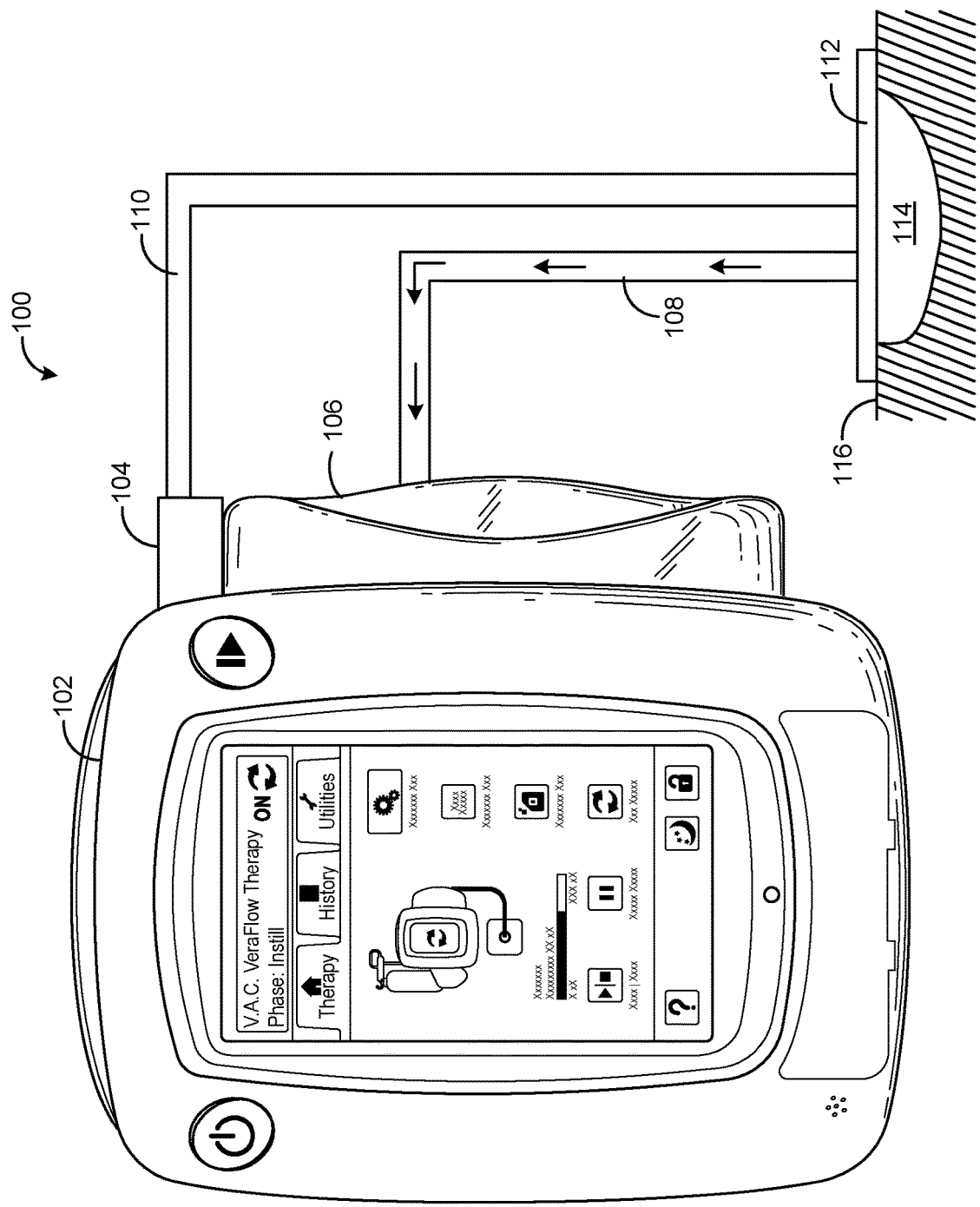
FIG. 1 is a block diagram of a wound therapy system including a therapy device coupled to a wound dressing via a primary conduit and a secondary conduit, according to an exemplary embodiment.
Figure 2:
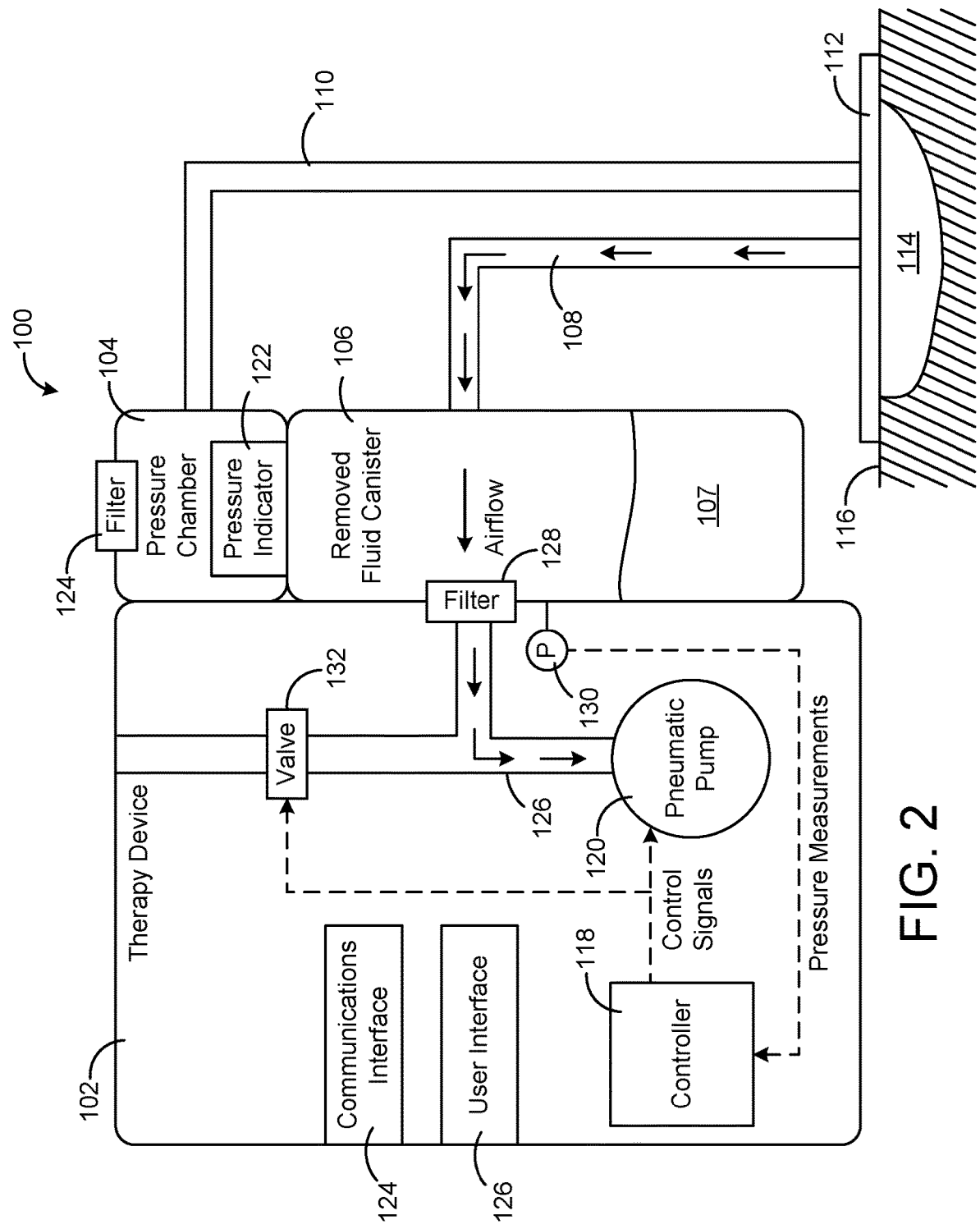
FIG. 2 is a block diagram illustrating the therapy device of FIG. 1 in greater detail and illustrating the operation of the therapy device to reduce pressure within a negative pressure circuit, according to an exemplary embodiment.
Figure 3:
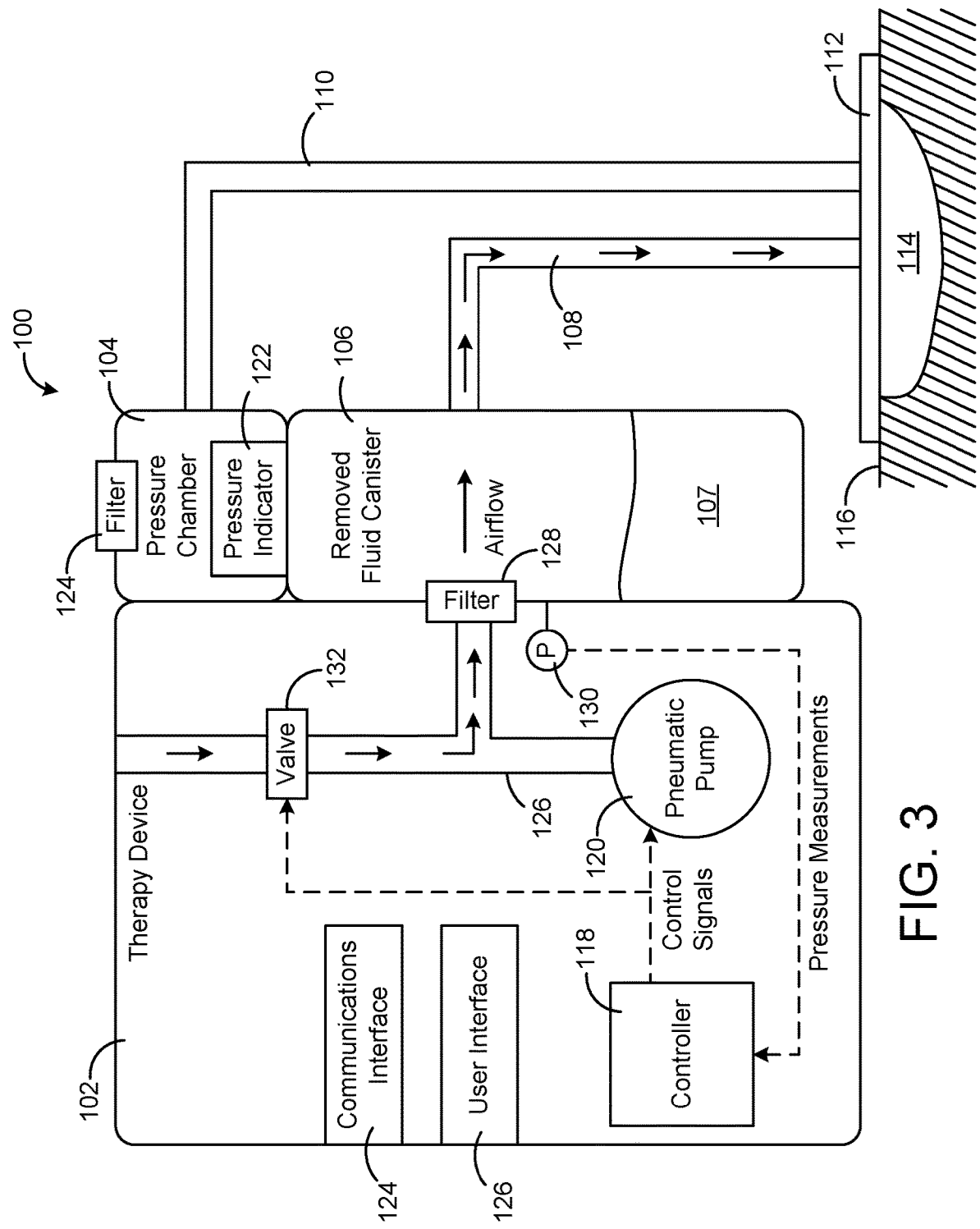
FIG. 3 is a block diagram illustrating the operation of the therapy device of FIG. 1 to vent the negative pressure circuit, according to an exemplary embodiment.

Referring to FIGS. 1-3, a negative pressure wound therapy (NPWT) system 100 is shown, according to an exemplary embodiment. NPWT system 100 is shown to include a therapy device 102 fluidly connected to a wound dressing 112 via a primary conduit 108 and a secondary conduit 110. Wound dressing 112 may be adhered or sealed to a patient's skin 116 surrounding a wound 114. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, U.S. patent application Ser. No. 14/087,418 filed Nov. 22, 2013, and U.S. Provisional Patent Application No. 62/650,132 filed Mar. 29, 2018. The entire disclosure of each of these patents and patent applications is incorporated by reference herein.

Therapy device 102 can be configured to provide negative pressure wound therapy by reducing the pressure at wound 114. Therapy device 102 can draw a vacuum at wound 114 (relative to atmospheric pressure) by removing fluids 107 such as wound exudate, air, and other fluids from wound 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound 114 may include instillation fluid previously delivered to wound 114. Instillation fluid can include, for example, a cleansing fluid, a prescribed fluid, a medicated fluid, an antibiotic fluid, or any other type of fluid which can be delivered to wound 114 during wound treatment. In some embodiments, therapy device 102 is configured to deliver instillation fluid to wound 114, as described in U.S. Provisional Patent Application No. 62/650,132 filed Mar. 29, 2018, the entire disclosure of which is incorporated by reference herein.

Fluids 107 removed from wound 114 pass through primary conduit 108 and are collected in removed fluid canister 106. Primary conduit 108 may have a first end coupled to removed fluid canister 106 and a second end coupled to the wound site (e.g., wound dressing 112). Removed fluid canister 106 may be a component of therapy device 102 configured to collect wound exudate and other fluids 107 removed from wound 114. In some embodiments, removed fluid canister 106 is detachable from therapy device 102 to allow canister 106 to be emptied and replaced as needed. A lower portion of canister 106 may be filled with wound exudate and other fluids 107 removed from wound 114, whereas an upper portion of canister 106 may be filled with air. Therapy device 102 can be configured to draw a vacuum within canister 106 by pumping air out of canister 106. The reduced pressure within canister 106 can be translated to wound dressing 112 and wound 114 via primary conduit 108 such that wound dressing 112 and wound 114 are maintained at the same pressure as canister 106.

Therapy device 102 is shown to include a pressure chamber 104. In some embodiments, pressure chamber 104 is attached to removed fluid canister 106 or located within removed fluid canister 106. However, the internal volume of pressure chamber 104 may be fluidly isolated from the internal volume of removed fluid canister 106. For example, removed fluid canister 106 may form a first chamber configured to contain removed fluid 107 and/or air pumped out of wound 114 via primary conduit 108, whereas pressure chamber 104 may form a second chamber fluidly isolated from the first chamber. Pressure chamber 104 may be fluidly connected to wound 114 via secondary conduit 110. Secondary conduit 110 may have a first end coupled to pressure chamber 104 and a second end coupled to the wound site (e.g., wound dressing 112) such that the negative pressure at the wound site is fluidly transmitted to pressure chamber 104 via secondary conduit 110.

Referring particularly to FIGS. 2-3, block diagrams illustrating therapy device 102 in greater detail are shown, according to an exemplary embodiment. Therapy device 102 is shown to include a pneumatic pump 120, a valve 132, a filter 128, and a controller 118. Pneumatic pump 120 can be fluidly coupled to removed fluid canister 106 (e.g., via conduit 126) and can be configured to draw a vacuum within canister 106 by pumping air out of canister 106. In some embodiments, pneumatic pump 120 is configured to operate in both a forward direction and a reverse direction. For example, pneumatic pump 120 can operate in the forward direction to pump air out of canister 106 and decrease the pressure within canister 106. Pneumatic pump 120 can operate in the reverse direction to pump air into canister 106 and increase the pressure within canister 106. Pneumatic pump 120 can be controlled by controller 118, described in greater detail below.

Filter 128 can be positioned between removed fluid canister 106 and pneumatic pump 120 (e.g., along conduit 126) such that the air pumped out of canister 106 passes through filter 128. Filter 128 can be configured to prevent liquid or solid particles from entering conduit 136 and reaching pneumatic pump 120. Filter 128 may include, for example, a bacterial filter that is hydrophobic and/or lipophilic such that aqueous and/or oily liquids will bead on the surface of filter 128. Pneumatic pump 120 can be configured to provide sufficient airflow through filter 128 that the pressure drop across filter 128 is not substantial (e.g., such that the pressure drop will not substantially interfere with the application of negative pressure to wound 114 from therapy device 102).

Valve 132 can be fluidly connected with pneumatic pump 120 and filter 128 via conduit 126. In some embodiments, valve 132 is configured to control airflow between conduit 126 and the environment around therapy device 102. For example, valve 132 can be opened to allow airflow into conduit 126, and closed to prevent airflow into conduit 126. Valve 132 can be opened and closed by controller 118. When valve 132 is closed, pneumatic pump 120 can draw a vacuum within a negative pressure circuit by causing airflow through filter 128 in a first direction, as shown in FIG. 2. The negative pressure circuit may include any component of system 100 that can be maintained at a negative pressure when performing negative pressure wound therapy (e.g., conduit 126, removed fluid canister 106, primary conduit 108, secondary conduit 110, wound dressing 112, and/or wound 114). When valve 132 is open, airflow from the environment around therapy device 102 may enter conduit 126 and fill the vacuum within the negative pressure circuit. The airflow from conduit 126 into canister 106 and other volumes within the negative pressure circuit may pass through filter 128 in a second direction, opposite the direction, as shown in FIG. 3.

In some embodiments, therapy device 102 includes one or more sensors. For example, therapy device 102 is shown to include a pressure sensor 130 configured to measure the pressure within canister 106 and/or the pressure at wound dressing 112 or wound 114. Pressure measurements recorded by pressure sensor 130 can be communicated to controller 118. Controller 118 use the pressure measurements to ensure that wound 114 is maintained at negative pressure. For example, controller 118 can activate pneumatic pump 120 in response to the pressure measurement from pressure sensor 130 exceeding a negative pressure setpoint in order to reduce the pressure at wound 114.

Figure 4A:
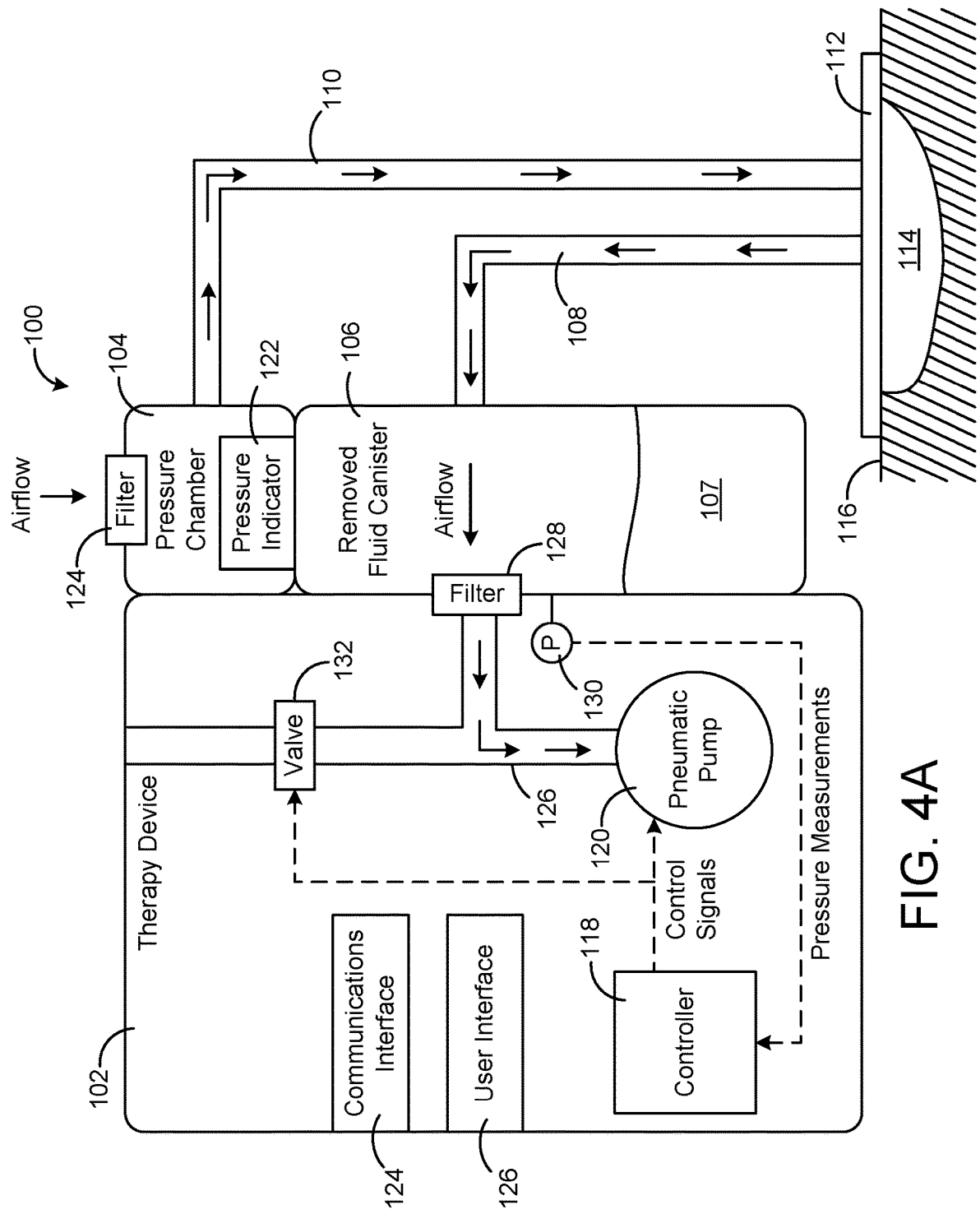
FIG. 4A is a block diagram illustrating the operation of the therapy device of FIG. 1 in the absence of a blockage and with a pressure indicator located within a pressure chamber, according to an exemplary embodiment.
Figure 4B:
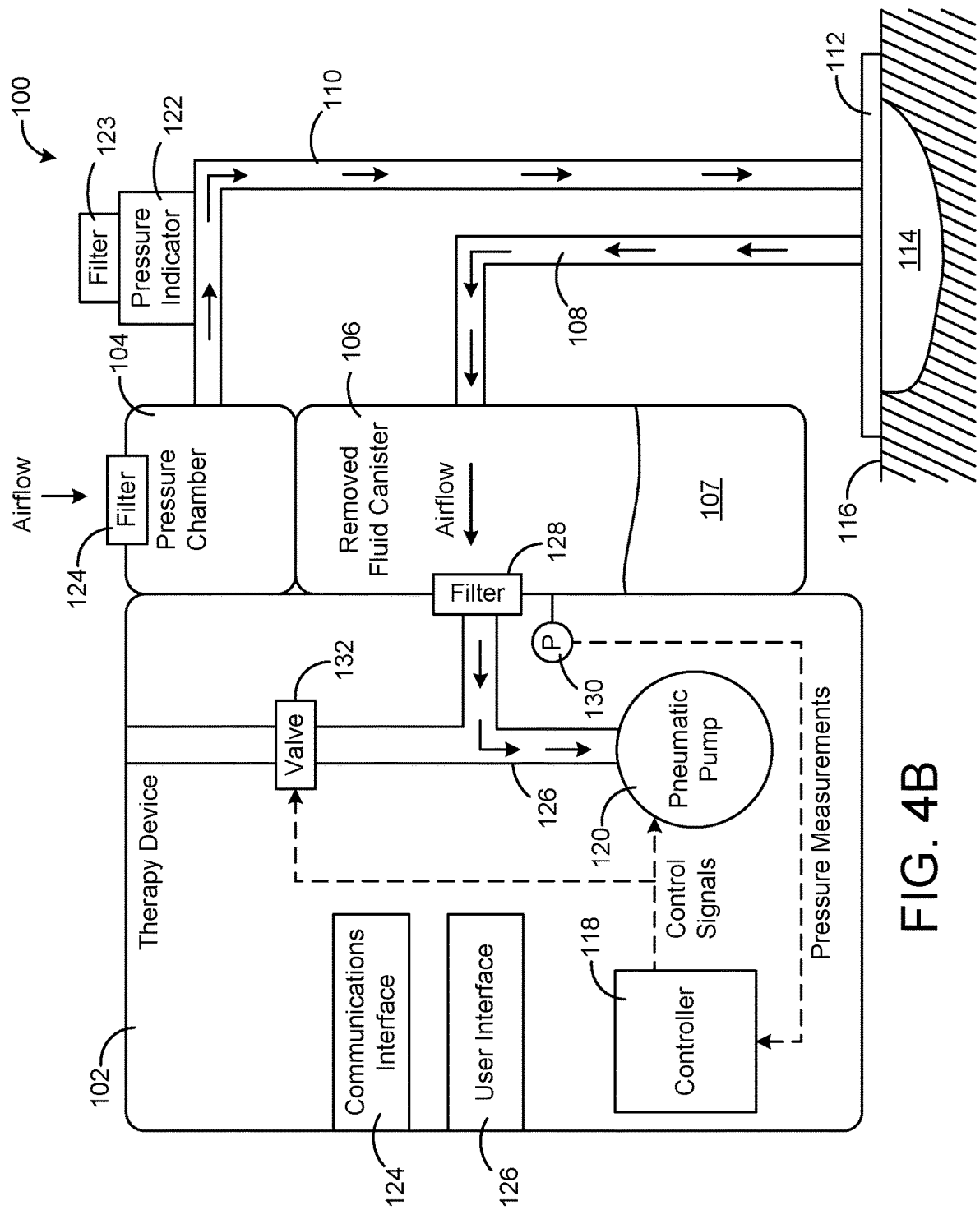
FIG. 4B is a block diagram illustrating the operation of the therapy device of FIG. 1 in the absence of a blockage and with the pressure indicator coupled to a secondary conduit coupled to the wound dressing, according to an exemplary embodiment.
Figure 5:
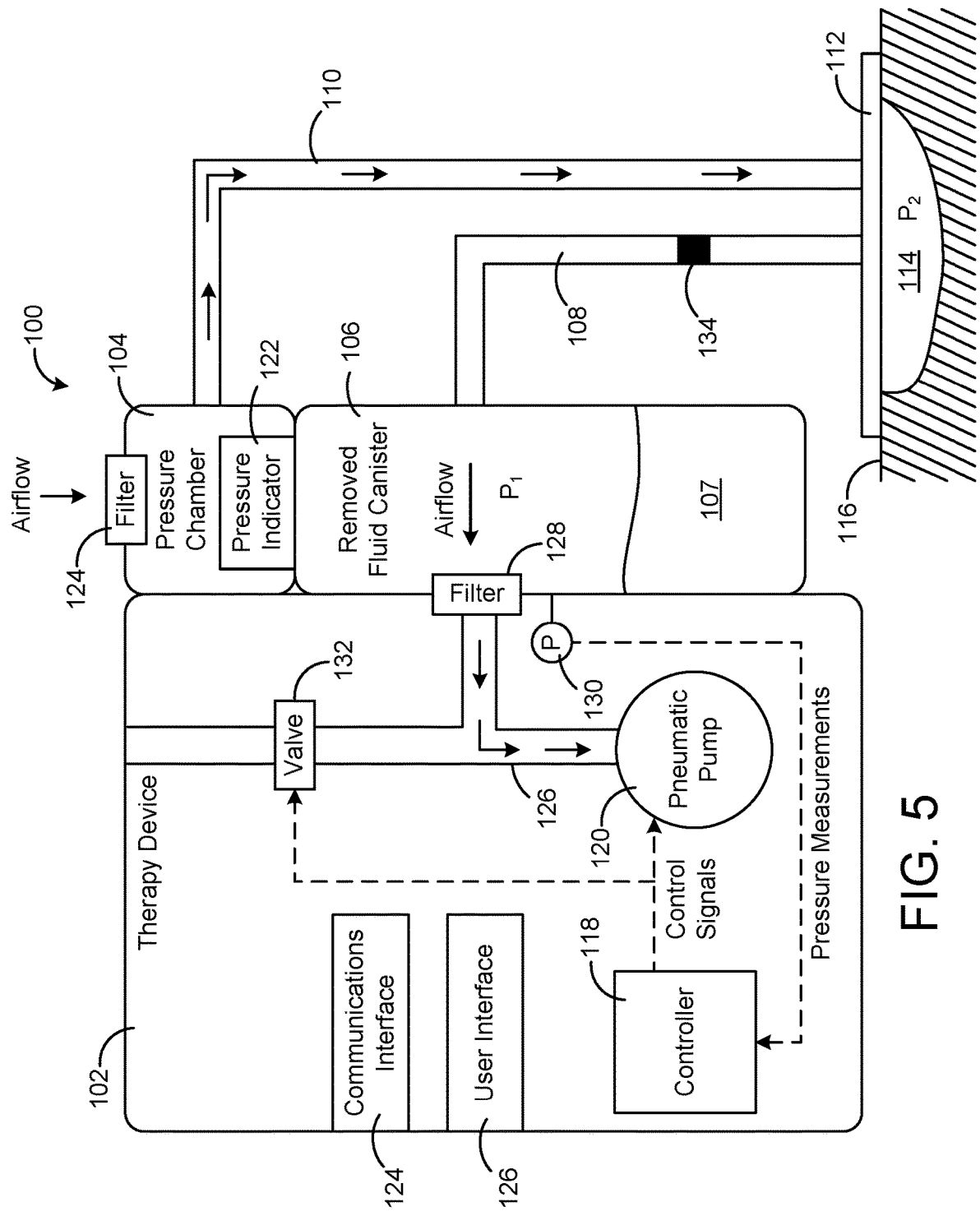
FIG. 5 is a block diagram illustrating the operation of the therapy device of FIG. 1 with a blockage in the primary conduit, according to an exemplary embodiment.

Referring now to FIGS. 4A-5, therapy device 102 is shown to include a pressure indicator 122. In various embodiments, pressure indicator 122 may be located within pressure chamber 104 (as shown in FIG. 4A) or positioned along secondary conduit 110 proximate pressure chamber 104 (as shown in FIG. 4B). Pressure indicator 122 may be an electronic pressure sensor, mechanical pressure indicator, or other pressure-sensitive device configured to sense and/or indicate the negative pressure at the location of pressure indicator 122 (e.g., within pressure chamber 104 and/or within secondary conduit 110). For example, pressure indicator 122 may include a bellows, a dial indicator, a holographic indicator, a spring-biased extensible indicator, an electronic pressure sensor, or any other type of mechanical or electronic pressure indicator.

Advantageously, pressure indicator 122 can be used to detect a blockage 134 (i.e., an occlusion, a clog, an obstruction, etc.) within primary conduit 108 and/or secondary conduit 110. When blockage 134 does not exist (as shown in FIG. 4), pressure chamber 104 and removed fluid canister 106 may equilibrate to the same pressure due to the fluid connections provided by primary conduit 108 and secondary conduit 110. Accordingly, the pressure within removed fluid canister 106 (i.e., the pressure measured by pressure sensor 130) may be equal to the pressure indicated by pressure indicator 122 in the absence of blockage 134. However, when blockage 134 exists (as shown in FIG. 5), the fluid connection between wound 114 and removed fluid canister 106 may be obstructed, which prevents pneumatic pump 120 from maintaining wound 114 at negative pressure. Accordingly, the pressure $P_1$ within removed fluid canister 106 may be different from the pressure $P_2$ at wound 114 (i.e., the pressure indicated by pressure indicator 122) when blockage 134 is present.

In some embodiments, pressure chamber 104 is configured to controllably leak air into the pressure chamber 104. The controlled leak of air may cause the negative pressure at the location of pressure indicator 122 to equilibrate to atmospheric pressure after blockage occurs 134. In some embodiments, pressure chamber 104 is configured to leak air into pressure chamber 104 at a controlled leak rate. This prevents the pressure within pressure chamber 104 from remaining fixed at the pressure that was present within pressure chamber 104 immediately before blockage 134 occurs. The controlled leak rate may be substantially less than the rate at which pneumatic pump 120 removes air from wound 114 such that the controlled air leak can be easily overcome by operating pneumatic pump 120 before blockage 134 occurs. In some embodiments, a filter 124 may be located along a wall of pressure chamber 104 and configured to leak air into pressure chamber 104 at the controlled leak rate. In other embodiments, filter 124 may be coupled to secondary conduit 110 (e.g., near an end of secondary conduit 110 proximate removed fluid canister 106) and configured to controllably leak air into secondary conduit 110. Similarly, a filter 123 (shown in FIG. 4B) can be configured to controllably leak air into pressure indicator 122 for embodiments in which pressure indicator 122 is coupled directly to secondary conduit 110.

In some embodiments, pressure indicator 122 is configured to physically deform or collapse responsive to the negative pressure at the location of pressure indicator 122. In some embodiments, pressure indicator 122 includes a plurality of individual sub-indicators. Each of the sub-indicators may be configured to physically deform or collapse at a different negative pressure such that the negative pressure at the location of pressure indicator 122 is indicated by which of the sub-indicators are physically deformed or collapsed. In some embodiments, each of the sub-indicators has a different thickness, causing each of the sub-indicators configured to physically deform or collapse at a different negative pressure.

In some embodiments, pressure indicator 122 is configured to indicate the negative pressure at the location of pressure indicator 122 relative to a plurality of pressure thresholds. The plurality of pressure thresholds may include at least a low pressure threshold and a high pressure threshold. Accordingly, pressure indicator 122 may indicate whether the negative pressure at the location of pressure indicator 122 is within a first negative pressure range below the low pressure threshold, within a second negative pressure range between the low pressure threshold and the high pressure threshold, and/or within a third negative pressure range above the high pressure threshold. In some embodiments, each of the negative pressure ranges corresponds to a different color visible on pressure indicator 122. For example, pressure indicator 122 may indicate a first color when the negative pressure at the location of pressure indicator 122 is within the first negative pressure range, a second color when the negative pressure at the location of pressure indicator 122 is within the second negative pressure range, and/or a third color when the negative pressure at the location of pressure indicator 122 is within a third negative pressure range.

In some embodiments, pressure indicator 122 is an electronic pressure sensor. Pressure indicator 122 may be coupled to secondary conduit 110 proximate removed fluid canister 106 and/or pressure chamber 104 and configured to sense the negative pressure within secondary conduit 110. Alternatively, pressure indicator 122 may be located within pressure chamber 104 and configured to measure the negative pressure within pressure chamber 104. For embodiments in which pressure indicator 122 is located within pressure chamber 104, therapy device 102 may include a bacterial filter located between pressure indicator 122 and secondary conduit 110 (e.g., along the surface of pressure chamber 110 where secondary conduit 110 connects to pressure chamber 104). In other embodiments, the bacterial filter may be located within secondary conduit 110.

In some embodiments, pressure indicator 122 includes a wireless communications interface configured to transmit pressure measurements recorded by pressure indicator 122. The pressure measurements can be transmitted to controller 118 or to an external system or device. In other embodiments, pressure indicator 122 may include a wired communications interface configured to transmit the pressure measurements to controller 118 or to an external system or device. In some embodiments, pressure indicator 122 is configured to compare the negative pressure at the location of pressure indicator 122 to one or more pressure thresholds and generate an alarm based on the negative pressure at the location of pressure indicator 122 relative to one or more pressure thresholds. Pressure indicator 122 can be configured to transmit the alarm to controller 118 and/or to an external system or device via the wired or wireless communications interface. In some embodiments, pressure indicator 122 includes a user interface and is configured to present the alarm to a user via the user interface. The user interface may include, for example, an electronic display configured to present the alarm visually, a speaker or sounder configured to present the alarm aurally, or any other type of interface device configured to indicate the alarm to a user.

Figure 6:
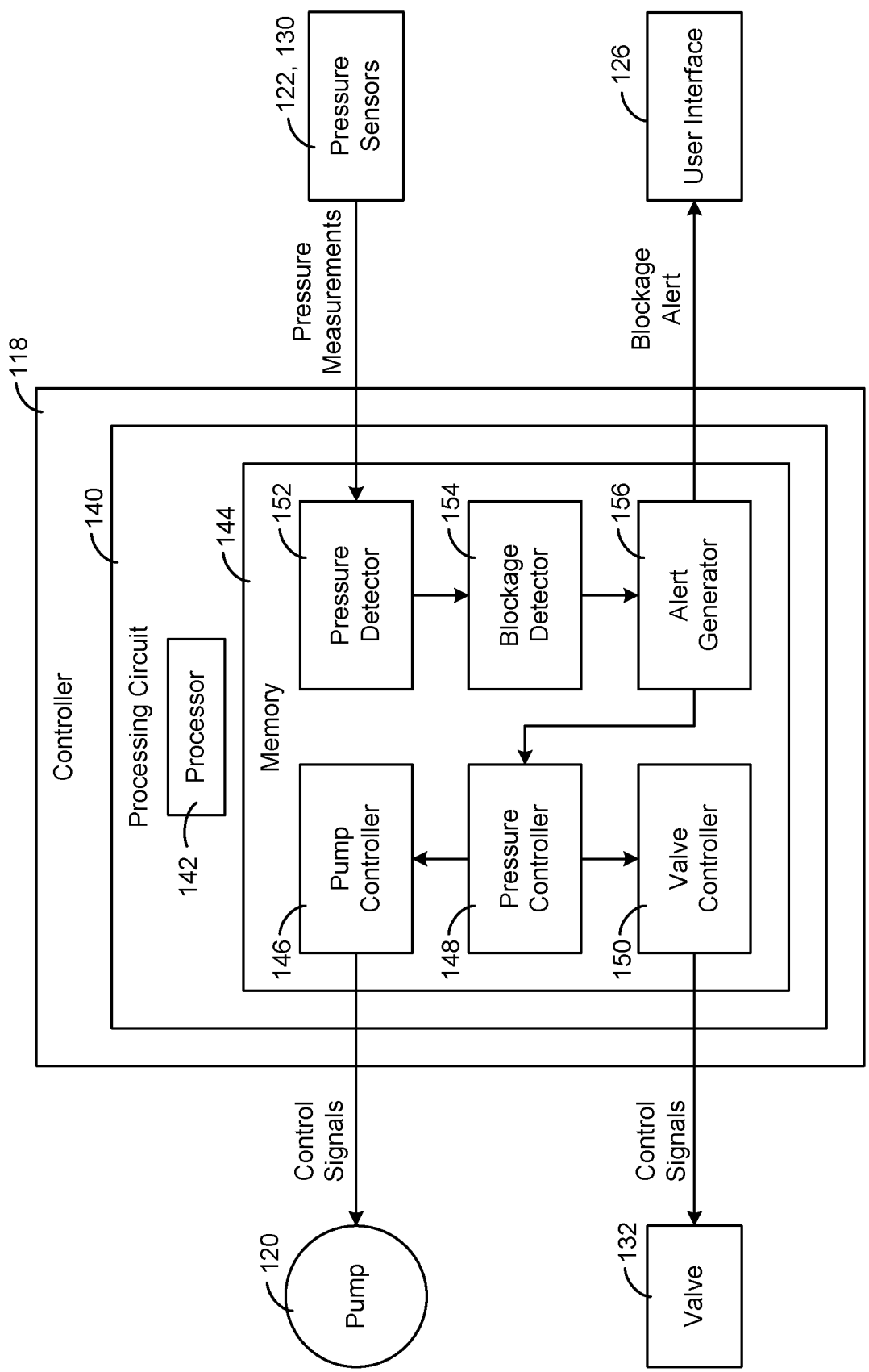
FIG. 6 is a block diagram illustrating a controller of the wound therapy device of FIG. 1 in greater detail, according to an exemplary embodiment.

In some embodiments, therapy device 102 includes a user interface 126. User interface 126 may include one or more buttons, dials, sliders, keys, or other input devices configured to receive input from a user. User interface 126 may also include one or more display devices (e.g., LEDs, LCD displays, etc.), speakers, tactile feedback devices, or other output devices configured to provide information to a user. In some embodiments, the pressure measurements recorded by pressure sensor 130 and/or pressure indicator 122 are presented to a user via user interface 126. User interface 126 can also display alerts generated by controller 118. For example, controller 118 can generate a "blockage detected" alert if a blockage is detected within secondary conduit 110. Controller Referring now to FIG. 6, a block diagram illustrating controller 118 in greater detail is shown, according to an exemplary embodiment. Controller 118 is shown to include a processing circuit 140 including a processor 142 and memory 144. Processor 142 may be a general purpose or specific purpose processor, an application specific integrated circuit (ASIC), one or more field programmable gate arrays (FPGAs), a group of processing components, or other suitable processing components. Processor 142 is configured to execute computer code or instructions stored in memory 144 or received from other computer readable media (e.g., CDROM, network storage, a remote server, etc.).

Memory 144 may include one or more devices (e.g., memory units, memory devices, storage devices, etc.) for storing data and/or computer code for completing and/or facilitating the various processes described in the present disclosure. Memory 144 may include random access memory (RAM), read-only memory (ROM), hard drive storage, temporary storage, non-volatile memory, flash memory, optical memory, or any other suitable memory for storing software objects and/or computer instructions. Memory 144 may include database components, object code components, script components, or any other type of information structure for supporting the various activities and information structures described in the present disclosure. Memory 144 may be communicably connected to processor 142 via processing circuit 140 and may include computer code for executing (e.g., by processor 142) one or more processes described herein. When processor 142 executes instructions stored in memory 144, processor 142 generally configures controller 118 (and more particularly processing circuit 140) to complete such activities.

Controller 118 is shown to include a pump controller 146, a valve controller 150, and a pressure controller 148. Pump controller 146 can be configured to operate pump 120 by generating and providing control signals to pump 120. The control signals provided to pump 120 can cause pump 120 to activate, deactivate, or achieve a variable capacity or speed (e.g., operate at half speed, operate at full speed, etc.). Similarly, valve controller 150 can be configured to operate valve 132 by generating and providing control signals to valve 132. The control signals provided to valve 132 can cause valve 132 to open, close, or achieve a specified intermediate position (e.g., one-third open, half open, etc.). In some embodiments, pump controller 146 and valve controller 150 are used by other components of controller 118 (e.g., pressure controller 148) to operate pump 120 and valve 132 when carrying out the processes described herein. For example, pressure controller 148 can use pump controller 146 and valve controller 150 to operate pump 120 and valve 132 to maintain the negative pressure at wound 114 at a negative pressure setpoint.

In some embodiments, pump controller 146 uses input from a canister sensor configured to detect whether removed fluid canister 106 is present. Pump controller 146 can be configured to activate pneumatic pump 120 only when removed fluid canister 106 is present. For example, pump controller 146 can check whether canister 106 is present and can activate pneumatic pump 120 in response to a determination that canister 106 is present. However, if canister 106 is not present, pump controller 146 may prevent pneumatic pump 120 from activating.

Controller 118 is shown to include a pressure detector 152, a blockage detector 154, and an alert generator 156. Pressure detector 152 may receive the pressure measurements from pressure sensor 130 and, for embodiments in which pressure indicator 122 is an electronic pressure sensor, pressure measurements from pressure indicator 122. In some embodiments, pressure detector 152 calculates a difference between the negative pressure $P_1$ measured by pressure sensor 130 and the negative pressure $P_2$ indicated by pressure indicator 122 (e.g., $\Delta P = P_1 - P_2$). In other embodiments, pressure detector 152 calculates a difference between the negative pressure $P_2$ indicated by pressure indicator 122 and a negative pressure threshold $P_{thresh}$ (e.g., $\Delta P = P_{thresh} - P_2$). In some embodiments, the negative pressure threshold $P_{thresh}$ is a pressure setpoint for the negative pressure at wound 114 or derived from the pressure setpoint.

Blockage detector 154 can be configured to detect blockage 134 within primary conduit 108 and/or secondary conduit 110. In some embodiments, blockage detector 154 receives the pressure difference $\Delta P$ calculated by pressure detector 152 and detects blockage 134 based on the pressure difference $\Delta P$. For example, blockage detector 154 can compare the pressure difference $\Delta P$ to a threshold and can detect that blockage 134 has occurred in response to the pressure difference $\Delta P$ exceeding the threshold. Blockage detector 154 can provide an indication of blockage 134 to alert generator 156. Alert generator 156 can generate a blockage alert and present the blockage alert to a user via user interface 126.

Flow Diagram

Figure 7:
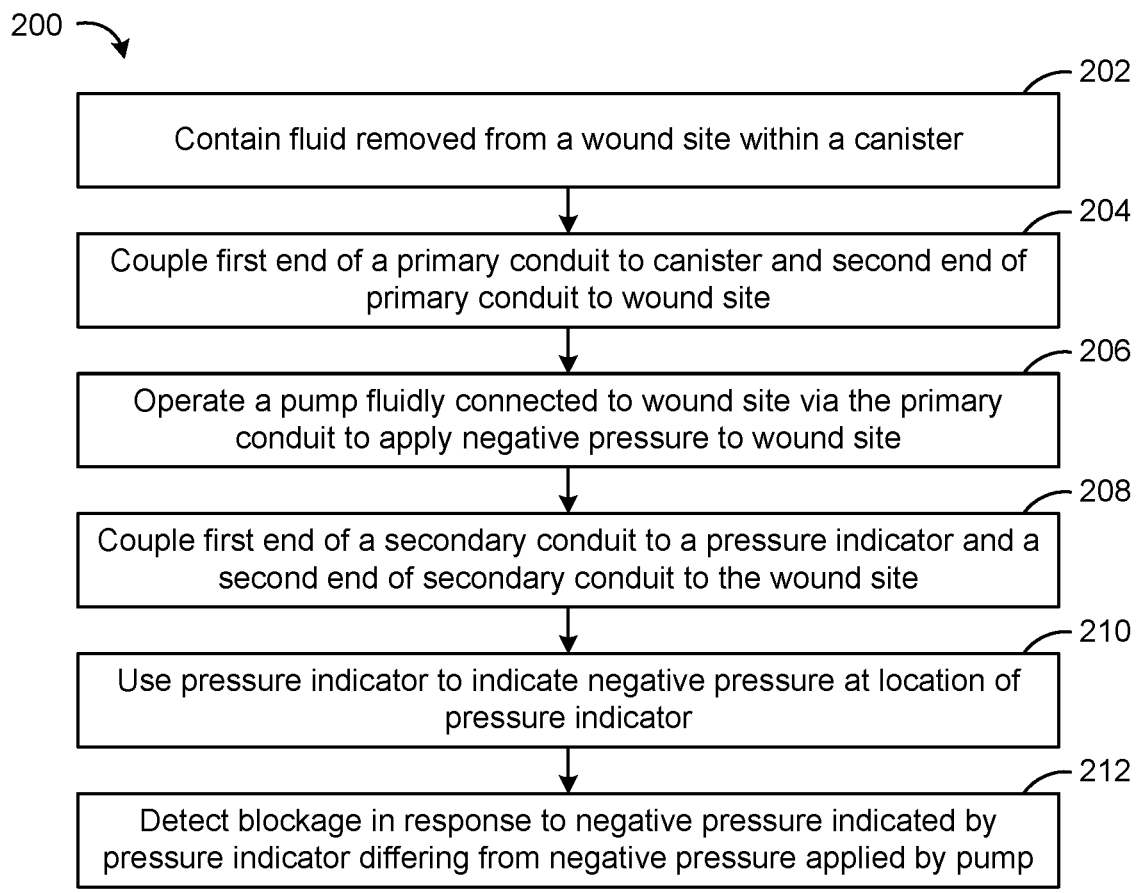
FIG. 7 is a flowchart of a process for detecting a blockage in a wound therapy system, according to an exemplary embodiment.

Referring now to FIG. 7, a flowchart of a process 200 for detecting a blockage in a wound therapy system is shown, according to an exemplary embodiment. Process 200 can be performed by one or more components of therapy device 102. For example, process 200 can be performed by controller 118, user interface 126, pneumatic pump 120, and/or other components of therapy device 102.

Process 200 is shown to include containing fluid 107 removed from a wound site within a canister 106 (step 202). A first end of a primary conduit 108 may be coupled to canister 106, whereas a second end of primary conduit 108 may be coupled to the wound site (step 204). Pneumatic pump 102 may be fluidly coupled to the wound site via primary conduit 108 and operated to apply negative pressure to the wound site via primary conduit 108 (step 206).

Process 200 is shown to include coupling a first end of a secondary conduit 110 to a pressure indicator 122 and a second end of secondary conduit 110 to the wound site (step 208). In some embodiments, step 208 includes coupling the second end of secondary conduit 110 directly to pressure indicator 122 (as shown in FIG. 4B). In other embodiments, step 208 includes coupling the second end of secondary conduit 110 to pressure chamber 104 and positioning pressure indicator 122 within pressure chamber 104 (as shown in FIG. 4A). After performing step 208, the negative pressure at the wound site is fluidly transmitted to pressure indicator 122 via secondary conduit 110 such that the negative pressure at the wound site is substantially equal to the negative pressure indicated by pressure indicator 122.

Process 200 is shown to include using the pressure indicator to indicate a negative pressure at the location of pressure indicator 122 (step 210). The negative pressure indicated by pressure indicator 122 may be substantially equal to the negative pressure applied by pneumatic pump 120 when blockage 134 is not present. However, the negative pressure indicated by pressure indicator 122 may differ from the negative pressure applied by pneumatic pump 120 when blockage is present. Accordingly, blockage 134 can be detected in response to the negative pressure indicated by pressure indicator 122 differing from the negative pressure applied by pneumatic pump 120 (step 212).

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A wound therapy system comprising:
   a canister including a first chamber configured to contain fluid removed from a wound site;
   a primary conduit having a first end coupled to the canister and a second end coupled to the wound site;
   a pump fluidly coupled to the wound site via the primary conduit and configured to apply negative pressure to the wound site via the primary conduit;
   a pressure indicator configured to indicate a negative pressure at the pressure indicator;
   a second chamber fluidly isolated from the first chamber, wherein the pressure indicator is located within the second chamber, and wherein the second chamber is configured to controllably leak air into the second chamber at a controlled leak rate; and
   a secondary conduit having a first end and a second end, the first end of the secondary conduit fluidly coupled to the pressure indicator and the second chamber, the second end of the secondary conduit coupled to the wound site such that the negative pressure at the wound site is fluidly transmitted to the pressure indicator and the second chamber via the secondary conduit;
   wherein a blockage in the primary conduit causes the negative pressure indicated by the pressure indicator to differ from the negative pressure applied by the pump, and wherein the pump is configured to remove the air from the second chamber via the secondary conduit and the primary conduit at an air removal rate greater than the controlled leak rate, causing the negative pressure at the pressure indicator to be substantially equal to the negative pressure applied by the pump before the blockage occurs.

2. The wound therapy system of claim 1, further comprising a filter located along a wall of the second chamber and configured to controllably leak air into the second chamber.

3. The wound therapy system of claim 1, further comprising a filter coupled to the first end of the secondary conduit proximate the canister and configured to controllably leak air into the secondary conduit.

4. The wound therapy system of claim 1, wherein the pressure indicator is configured to physically deform or collapse responsive to the negative pressure at the pressure indicator.

5. The wound therapy system of claim 4, wherein the pressure indicator comprises a plurality of individual sub-indicators, each of the sub-indicators configured to physically deform or collapse at a different negative pressure such that the negative pressure at the pressure indicator is indicated by which of the sub-indicators are physically deformed or collapsed.

6. The wound therapy system of claim 1, wherein the pressure indicator is configured to indicate the negative pressure at the pressure indicator relative to a plurality of pressure thresholds.

7. The wound therapy system of claim 6, wherein the plurality of pressure thresholds comprise at least a low pressure threshold and a high pressure threshold such that the pressure indicator indicates whether the negative pressure at the pressure indicator is:
within a first negative pressure range below the low pressure threshold;
within a second negative pressure range between the low pressure threshold and the high pressure threshold; and
within a third negative pressure range above the high pressure threshold.

8. The wound therapy system of claim 7, wherein each of the negative pressure ranges corresponds to a different color visible on the pressure indicator such that the pressure indicator indicates:
a first color when the negative pressure at the pressure indicator is within the first negative pressure range;
a second color when the negative pressure at the pressure indicator is within the second negative pressure range; and
a third color when the negative pressure at the pressure indicator is within a third negative pressure range.

9. The wound therapy system of claim 1, wherein the pressure indicator is an electronic pressure sensor coupled to the first end of the secondary conduit proximate the canister and configured to sense the negative pressure within the secondary conduit.

10. The wound therapy system of claim 9, wherein the pressure indicator is configured to compare the negative pressure at the pressure indicator to one or more pressure thresholds and generate an alarm based on the negative pressure at the pressure indicator relative to one or more pressure thresholds.

11. The wound therapy system of claim 10, wherein the pressure indicator comprises a wireless communications interface and is configured to transmit the alarm to an external system or device via the wireless communications interface.

12. A method for detecting a blockage in a wound therapy system, the method comprising:
containing fluid removed from a wound site within a first chamber of a canister;
coupling a first end of a primary conduit to the canister and a second end of the primary conduit to the wound site;
operating a pump fluidly coupled to the wound site via the primary conduit to apply negative pressure to the wound site via the primary conduit;
providing a second chamber fluidly isolated from the first chamber;
locating a pressure indicator within the second chamber;
coupling a first end of a secondary conduit to the pressure indicator and to the second chamber, and a second end of the secondary conduit to the wound site such that the negative pressure at the wound site is fluidly transmitted to the pressure indicator and the second chamber via the secondary conduit;
using the pressure indicator to indicate a negative pressure at the pressure indicator; and
detecting the blockage in response to the negative pressure indicated by the pressure indicator differing from the negative pressure applied by the pump;
wherein air controllably leaks into the second chamber at a controlled leak rate, and wherein operating the pump removes the air from the second chamber via the secondary conduit and the primary conduit at an air removal rate greater than the controlled leak rate, causing the negative pressure at the pressure indicator to be substantially equal to the negative pressure applied by the pump before the blockage occurs.

13. The method of claim 12, further comprising coupling a filter to the first end of the secondary conduit proximate the canister and controllably leaking the air into the secondary conduit via the filter.

14. The method of claim 12, wherein the pressure indicator is an electronic pressure sensor coupled to the first end of the secondary conduit proximate the canister that senses the negative pressure within the secondary conduit.

15. The method of claim 14, further comprising:
comparing the negative pressure at the pressure indicator to one or more pressure thresholds; and
generating an alarm based on the negative pressure at the pressure indicator relative to one or more pressure thresholds.

16. The method of claim 15, further comprising transmitting the alarm to an external system or device via a wireless communications interface of the pressure indicator.

17. The method of claim 15, further comprising presenting the alarm to a user via a user interface of the pressure indicator.

18. The method of claim 17, wherein presenting the alarm to the user comprises at least one of:
presenting the alarm visually via an electronic display of the user interface; or
presenting the alarm aurally via a speaker or sounder of the user interface.

19. A wound therapy system comprising:
a canister including a first chamber configured to contain fluid removed from a wound site;
a primary conduit having a first end coupled to the canister and a second end coupled to the wound site;
a pump fluidly coupled to the wound site via the primary conduit and configured to apply negative pressure to the wound site via the primary conduit;
a pressure indicator configured to indicate a negative pressure at the pressure indicator and to physically deform or collapse responsive to the negative pressure, wherein the pressure indicator comprises a plurality of individual sub-indicators, each of the sub-indicators configured to physically deform or collapse at a different negative pressure such that the negative pressure at the pressure indicator is indicated by which of the sub-indicators are physically deformed or collapsed;
a second chamber fluidly isolated from the first chamber; and
a secondary conduit having a first end and a second end, the first end of the secondary conduit fluidly coupled to the pressure indicator and the second chamber, the second end of the secondary conduit coupled to the wound site such that the negative pressure at the wound site is fluidly transmitted to the pressure indicator and the second chamber via the secondary conduit;
wherein a blockage in the primary conduit causes the negative pressure indicated by the pressure indicator to differ from the negative pressure applied by the pump.

* * * * *